US012685469B2

(12) United States Patent
Sundaresan et al.

(10) Patent No.: US 12,685,469 B2
(45) Date of Patent: Jul. 21, 2026

(54) SYSTEM AND METHOD TO DYNAMICALLY ASSESS AND REDUCE USER MENTAL STRAIN WHEN OPERATING INFORMATION HANDLING SYSTEMS

(71) Applicant: Dell Products L.P., Round Rock, TX (US)

(72) Inventors: Vivek Sundaresan, Bangalore (IN); Akash L, Bangalore (IN); Karthik Venkatesh, Bangalore (IN)

(73) Assignee: Dell Products L.P., Round Rock, TX (US)

( * ) Notice: Subject to any disclaimer, the term of this patent is extended or adjusted under 35 U.S.C. 154(b) by 455 days.

(21) Appl. No.: 18/140,081

(22) Filed: Apr. 27, 2023

(65) Prior Publication Data

US 2024/0358302 A1     Oct. 31, 2024

(51) Int. Cl.
*A61B 5/16*          (2006.01)
(52) U.S. Cl.
CPC .................................... *A61B 5/163* (2017.08)

(58) Field of Classification Search
None
See application file for complete search history.

(56) References Cited

U.S. PATENT DOCUMENTS

| | | | |
|---|---|---|---|
| 9,201,512 B1 * | 12/2015 | Raffle ...................... | G06F 3/033 |
| 10,838,132 B1 * | 11/2020 | Calafiore ............. | G02B 6/0015 |
| 10,842,430 B1 * | 11/2020 | Novelli ................... | G06F 3/013 |
| 2008/0074618 A1 * | 3/2008 | Qi ......................... | A61B 5/1103 |
| | | | 351/221 |
| 2008/0088646 A1 * | 4/2008 | Sako .................. | G02B 27/0172 |
| | | | 345/647 |
| 2020/0309594 A1 * | 10/2020 | Wei ........................ | H10F 39/803 |

* cited by examiner

*Primary Examiner* — Michael R Bloch
(74) *Attorney, Agent, or Firm* — Terrile, Cannatti & Chambers, LLP; Emmanuel A. Rivera

(57) ABSTRACT

A system, method, and computer-readable medium for assessing and reducing mental strain of a user when the user operates an information handling system comprising. Sensors of the information handling system's display capture light that is reflected from an eye of the user. The captured light is converted to voltage values over time. The voltage values are correlated to eye movement or blinking. If the eye movement or blinking meets or exceeds a threshold value, corrective action is taken to reduce mental strain of the user.

18 Claims, 8 Drawing Sheets

200

Start
202

Define Perimeter Of Light From Screen Reflected to Sensor
204

Sensor Captures Reflected Light
206

Analyze Light Intensity Differences From Reflected Light and Convert to Voltage Value
208

If Fatigue Value (VAS) Close to Threshold, Warn User
210

Alert OS To Take Corrective Action
212

Provide Corrective Action Options or Use Default Action
214

End
216 detection rate, %

100
80
60
40
20
0

○ User 1
◐ User 2
● User 3
⊜ User 4
⊕ All User

50%    60%    70%    80%    90%    100%
thresholds
402

404

| Monitoring Mode 11XX | Trigger Pts 11xx | Engagement by "Microservice 126" 11xx | | | Resolution by "Microservice 126" 11xx |
|---|---|---|---|---|---|
| | | Level 1 | Level 2 | Level 3 | |
| Light 11xx | | Notify the user and allow snooze by the user | Notify the user and allow snooze by the user | Notify the user but don't allow snooze. Force the user for any option listed to perform | Screen resolution will be made 25% bigger and stop further actions. Even we can reduce screen brightness. Reset the VAS fatigue value back to 0 |
| Medium 11xx | when the VAS fatigue value is >= user threshold | Notify the user and allow snooze by the user | Notify the user but don't allow snooze. Force the user for any option listed to perform | | Start a timer of 60 seconds and lock the screen post 60 seconds. Reset the VAS fatigue value back to 0 |
| High 11xx | | Notify the user but don't allow snooze. Force the user for any option listed to perform | | | Lock the screen and start a microservice inbuilt timer for 5 minutes. Only after the post microservice timer expiry, the user will be able to key in the password to log in back. Reset the VAS fatigue value back to 0 |
| | | Snooze default time = 3 minutes | Snooze default time = 3 minutes | Snooze default time = 3 minutes | |

SYSTEM AND METHOD TO DYNAMICALLY ASSESS AND REDUCE USER MENTAL STRAIN WHEN OPERATING INFORMATION HANDLING SYSTEMS

BACKGROUND OF THE INVENTION

Field of the Invention

The present invention relates to information. More specifically, embodiments of the invention provide a system, method, and computer-readable medium for assessing and reducing mental strain of users when operating information handling systems.

Description of the Related Art

As the value and use of information continues to increase, individuals and businesses seek additional ways to process and store information. One option available to users is information handling systems. Information handling systems include personal computers (PC), server computers, such as desktops. An information handling system generally processes, compiles, stores, and/or communicates information or data for business, personal, or other purposes thereby allowing users to take advantage of the value of the information. Because technology and information handling needs and requirements vary between different users or applications, information handling systems may also vary regarding what information is handled, how the information is handled, how much information is processed, stored, or communicated, and how quickly and efficiently the information may be processed, stored, or communicated. The variations in information handling systems allow for information handling systems to be general or configured for a specific user or specific use such as financial transaction processing, airline reservations, enterprise data storage, or global communications. In addition, information handling systems may include a variety of hardware and software components that may be configured to process, store, and communicate information and may include one or more computer systems, data storage systems, and networking systems.

The use of information handling systems is pervasive in daily work and leisure activities. Extended and overuse of information handling systems can lead to health issues, including mental issues. Too much screen time can not only affect physical and mental health, but can lead to decreased efficiency. In certain instances, overuse can lead to serious accidents.

Monitoring the use of information handling systems, and particularly screen time spent by users should be performed as to the effects on users. Measuring of physiological signals related to fatigue and stress should be performed in real time, without interfering with user efficiency. In addition, it would be desirable to have such monitoring performed without users taking proactive and intrusive measures, such as wearing monitoring devices.

SUMMARY OF THE INVENTION

A computer-implementable method, system and computer-readable storage medium for assessing and reducing mental strain of a user when operating an information handling system comprising capturing reflected light from an eye of the user by one or more sensors of the information handling system; converting the captured light to voltage values over time; correlating the voltage values over time to eye movement or blinking; and taking corrective action if eye movement or blinking meet or exceed a fatigue threshold.

BRIEF DESCRIPTION OF THE DRAWINGS

The present invention may be better understood, and its numerous objects, features and advantages made apparent to those skilled in the art by referencing the accompanying drawings. The use of the same reference number throughout the several figures designates a like or similar element.

FIG. 11 is a chart of microservice interaction based on different levels of monitoring.

DETAILED DESCRIPTION

Described herein are implementations that provide for monitoring of a user's mental strain level, and notifying the user when the mental strain level reaches a determined threshold limit. A message can be provided to the user and the user can take corrective action. If the user neglects the message and the mental strain level increases, action can automatically be taken to reduce and prevent increase of the user mental strain.

Implementations make use of sensors with dye-sensitized photoelectric cells. The sensors are included on a screen (e.g., display) of an information handling system, such as a laptop computer, and can operate without a power source. The sensors are used to pick up and measure light reflected from a user's eye. The measured light can be translated to a fatigue index of the user.

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communicating with external devices as well as various input and output (I/O) devices, such as a microphone, keyboard, a video display, a mouse, etc. The information handling system may also include one or more buses operable to transmit communications between the various hardware components.

Figure 1:
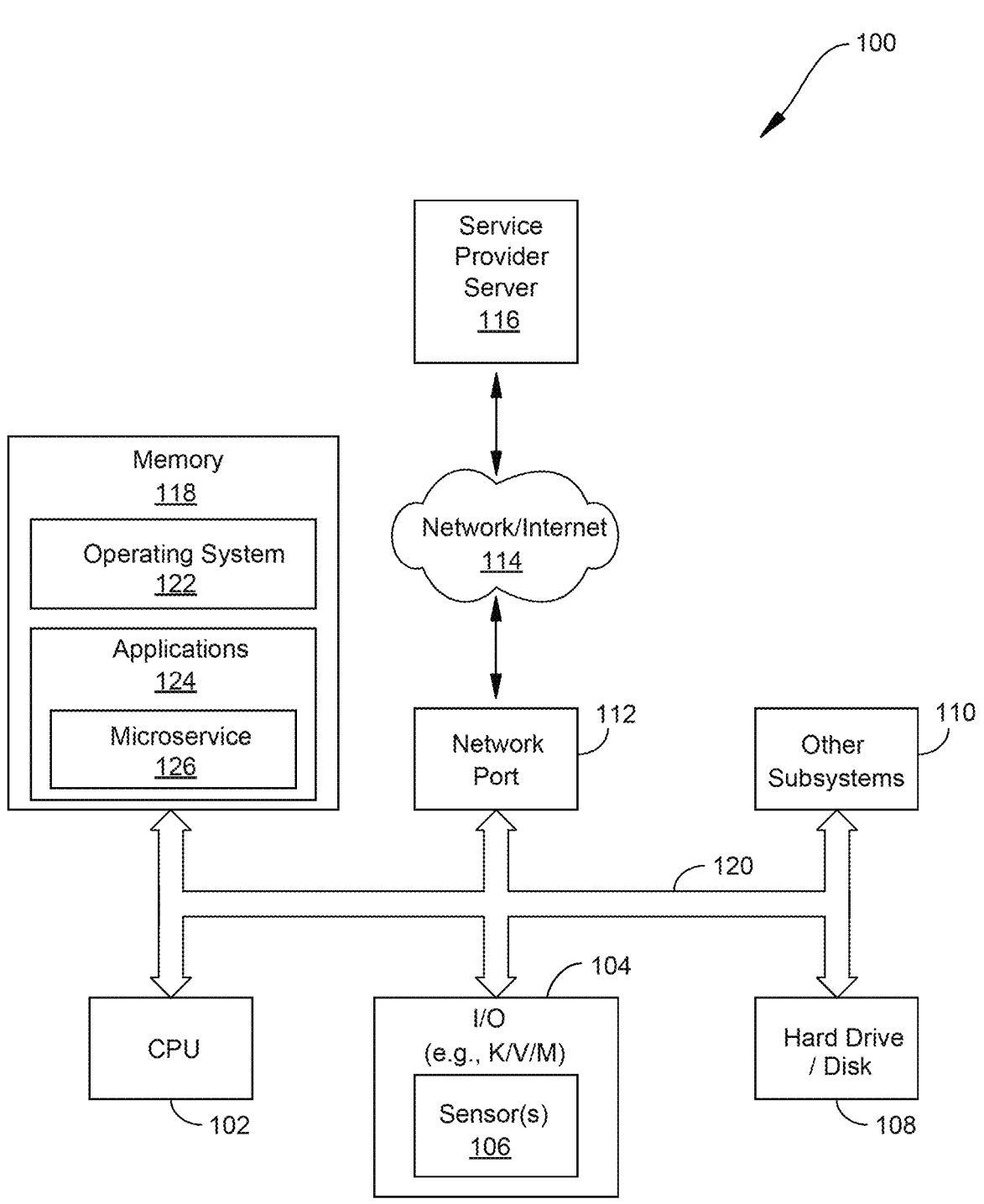
FIG. 1 is general illustration of components of an information handling system.

FIG. 1 is a generalized illustration of an information handling system 100 that can be used to implement the system and method of the present invention. The information handling system 100 can be configured for example as a laptop computer, desktop computer, tablet, smart phone, etc.

The information handling system 100 includes a processor (e.g., central processor unit or "CPU") 102, input/output (I/O) devices 104, such as a microphone, a keyboard, a video/display, a mouse, and associated controllers (e.g., K/V/M). In particular, the I/O devices 104 can include sensor(s) 106 that use dye-sensitized photoelectric cells, and are used to pick up and measure reflected light from a user's eye as further described herein. In certain implementations, the sensor(s) 106 are integrated into a display of the information handling system, such as built display of a laptop computer, or an external display/monitor of a desktop computer.

The information handling system 100 includes a hard drive or disk storage 108, and various other subsystems 110. In various embodiments, the information handling system 100 also includes network port 112 operable to connect to a network 114, where network 114 can include one or more wired and wireless networks, including the Internet. Network 114 is likewise accessible by a service provider server 116.

The information handling system 100 likewise includes system memory 118, which is interconnected to the foregoing via one or more buses 120. System memory 118 can be implemented as hardware, firmware, software, or a combination of such. System memory 118 further includes an operating system (OS) 122. Embodiments provide for the system memory 118 to include applications 124. Various implementations provide a microservice application 126 included in applications 124. The microservice application 126 is further described herein and is configured to perform certain processes.

Figure 2:
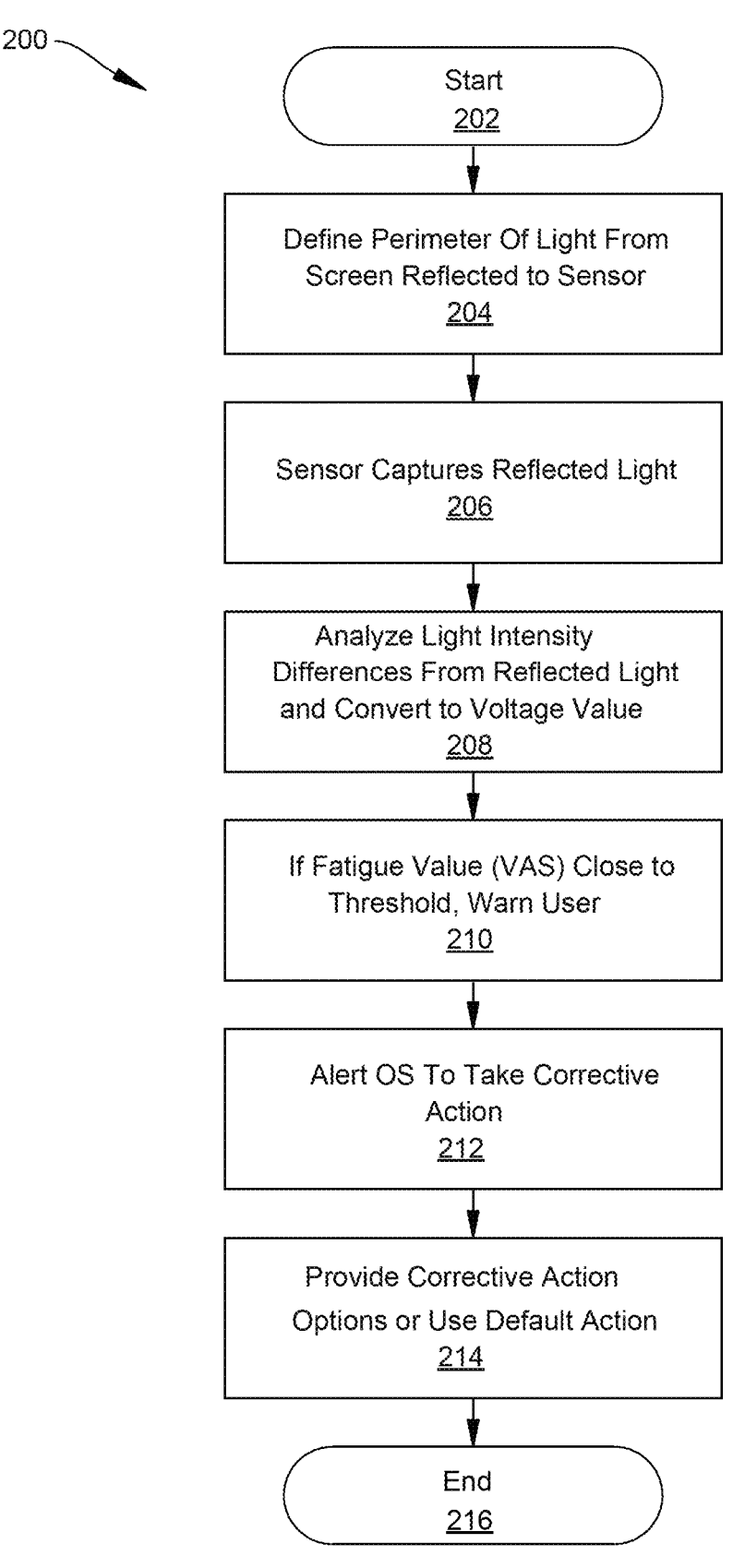
FIG. 2 is a generalized flowchart for workflow of the stages of the present invention.

FIG. 2 is a generalized flowchart 200 for workflow of the stages described herein. The order in which the flowchart 200 is described is not intended to be construed as a limitation, and any number of the described steps may be combined in any order to implement the workflow. The stages of flowchart 200 are further described herein. The flowchart 200 may be implemented in any suitable hardware, software, firmware, or a combination thereof, without departing from the scope of the invention.

At step 202, the flowchart 200 starts. At stage 204, the perimeter of light generated by a display is defined. The light that is generated is capable of being reflected back from a user's eye to the sensor(s) 106. The display can be an integrated or external display to an information handling system 100. The display is the display that a user looks at while using the information handling system 100.

At stage 206, the reflected light from a user's eye is captured by sensor(s) 106. At stage 208, light intensity differences from the reflected light are analyzed. The analyzed light is converted to voltage values and processed to determine eye movement and eye blinking.

At stage 210, if a determined fatigue value is close to a threshold value, the user is warned by the microservice 126. Corrective action messages can be provided to the user to take action. The fatigue value can be based on the visual analog scale or VAS. VAS being an industry wide standard that is a validated, subjective measure for acute and chronic pain that is marked over a continuum between "no pain" and "worst pain." VAS results can be obtained through fatigue evaluation as determined at stage 208.

At stage 212, if the fatigue value crosses beyond a set threshold limit, the microservice 126 can alert the operating system 122 to take corrective action on the information handling system 100. At stage 214, the operating system 122 can provide a message to the user as to corrected actions that can be chosen by the user. If the user does not select an action by a predetermined time, a default action can be taken by the microservice 126/operating system 122. At step 216, the flowchart 200 ends.

Figures 3, 4:
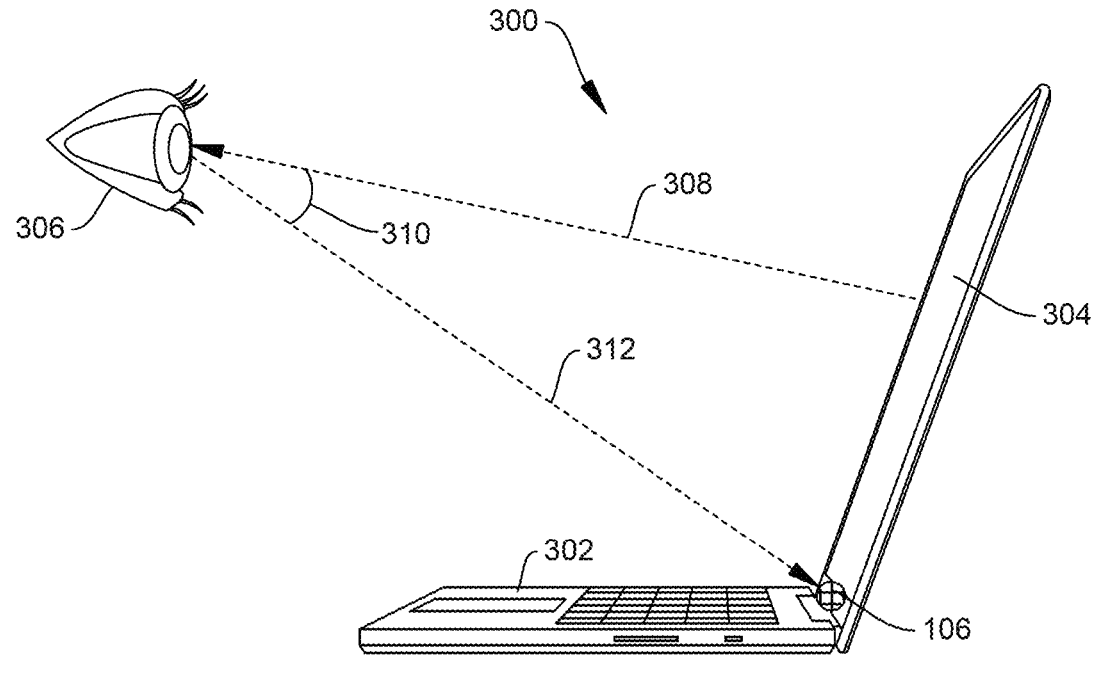
FIG. 3 is a simplified diagram that represents defining perimeter of light from a display.
FIG. 4 is a graph of detection rate for spontaneous blinks using voltage change rate.

FIG. 3 shows a diagram 300 that represents defining perimeter of light from a display. The diagram 300 shows a laptop computer 302 which can be an information handling system 100 with a display 304. Display 304 generating light. In this stage, the microservice 126 can be trained with an initial dataset that defines the intensity/energy of light intensity that captured by the sensor 106 which is reflected from the eye 306 of the user. This can be determined by analyzing the intensity of light 308 being emitted from the screen of the display 304 and based on the facial position of the user which determines the angle of incidence 310 of light 312 being reflected by the eye 306. Maximum distance can be defined within which the user's facial position should be from the screen for accurate analysis of output by microservice 126. The sensor(s) 106 can determine the intensity of light emitted from the screen, and can determine the intensity light that is reflected from the eye 306. Therefore, the sensor(s) 106 captures reflected light falling within the range of light emitted from the screen and light reflected from the eye 306.

At stage 206 of FIG. 2, the light reflected 312 from the user's eye 306 is captured by the sensor(s) 106. The dye-sensitized photoelectric cells in the sensor(s) 106 can detect differences in the light intensity reflected from the user's eye 306 (e.g., pupil, white of eye, and eyelid).

It is desirable to determine a fatigue index of the user. By detecting differences in the light intensity classification can be performed as user's eye state as opened, blinking, or closed states. This enables us to detect the drowsiness conditions of the users. Based on the blinking of eye frequency, duration of eyes in the open state and closed state, a threshold value can be calculated as to fatigue index.

At stage 208 of FIG. 2, light intensity differences are converted into a voltage value that is processed to deduce eye 306 movements and blinking. Implementations can include initially providing the microservice 126, known medical suggested data for spontaneous blinking. For example, generally a person on average blinks 12 times per minute. It is desired to detect a user's spontaneous blinking for the microservice 126.

Based on medically suggested data, a threshold is set for voluntary blinking, which for example can be translated to 70% of the voltage change rate. Since there can be a different duration for each spontaneous blink, threshold can be calculated for a user by monitoring the user's spontaneous blinking which can be captured in training data. The initial value can be calculated based on the following equation.

$$\text{Detection rate } (\%) = \frac{\text{Detected Blinks of User by Sensor(s)}}{\text{Average Medically Determined Blinks}} \times 100$$

FIG. 4 shows a graph 400 of detection rate for spontaneous blinks using voltage change rate. Threshold percentages 402 of 50% to 100% are plotted against detection rate percentages 404. For example, higher detection rate percentages are seen with lower threshold percentages, with a threshold percentage of 50% showing highest spontaneous blink detection rate percentages near 100%. Implications are that threshold percentage values less than 50% can include false-positive detection errors due to signal noise. Graph 400 shows that threshold percentage values of 60% detect about 90% of all spontaneous blinks without false-positive detection errors. Therefore, the threshold percentage values of 60% should be adequate for acquiring a user's spontaneous blinks, while 70% is suitable for voluntary blinks.

Figure 5:
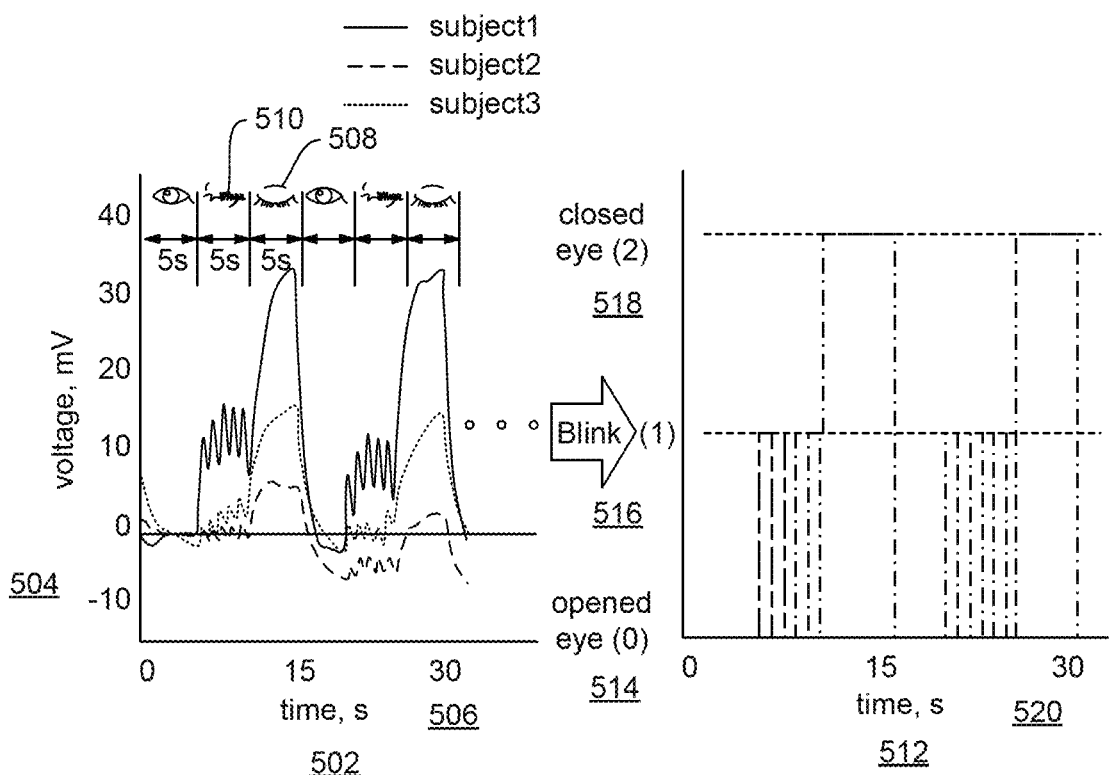
FIG. 5 are graphs related to user's blink duration or eye closure time.

FIG. 5 shows graphs related to user's blink duration or eye closure time. In addition to spontaneous blinking, blink duration or eye closure time can provide another indicator of a user's alertness. Blink duration can be indicative of symptom of a user's increased drowsiness.

Graph 502 plots voltage 504 over time 506. For example, the voltage value at closed eye 508 is higher than the voltage value of blinked eye 510, which can distinguish a closed eye state from a blinked eye state. Graph 512 summarizes and classifies states from graph 502 plots output voltage values of class 0 "opened eye" state 514, class 1 "blinked eye" state 516, and class 2 "closed eye" state 518 over time 520.

At stage 210 of FIG. 2, the graphs and data of stage 208 are further analyzed. Implementations provide for the microservice 126 to generate typical output voltage values for blink duration of a user over a different period, such as when the user is active, tired, strained, etc. Blink duration with various time lengths can be determined.

Figure 6:
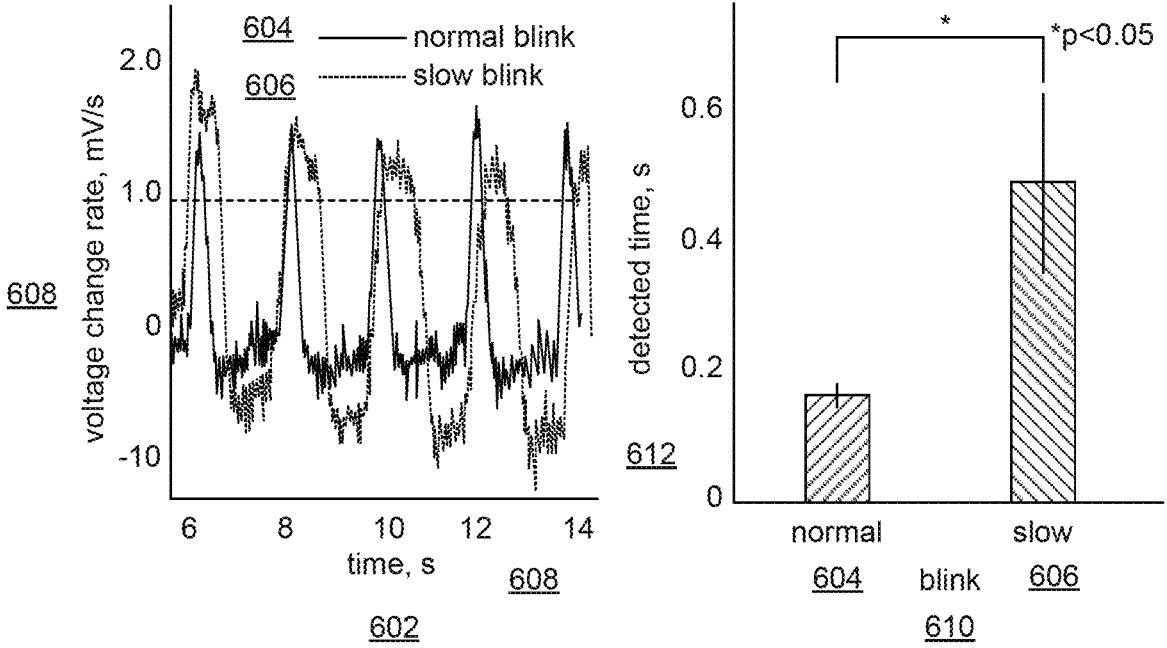
FIG. 6 is a graph of normal blink and slow blink voltage values over time.

FIG. 6 shows a graph 602 of normal blink 604 and slow blink 606 voltage values 608 over time 610. Graph 610 shows significant time 612 differences of normal blink 604 and slow blink 606. Therefore, based on time duration, microservice 126 can distinguish between blink duration types (i.e., normal blink versus slow blink). In addition, blink burst can also be analyzed.

Figure 7:
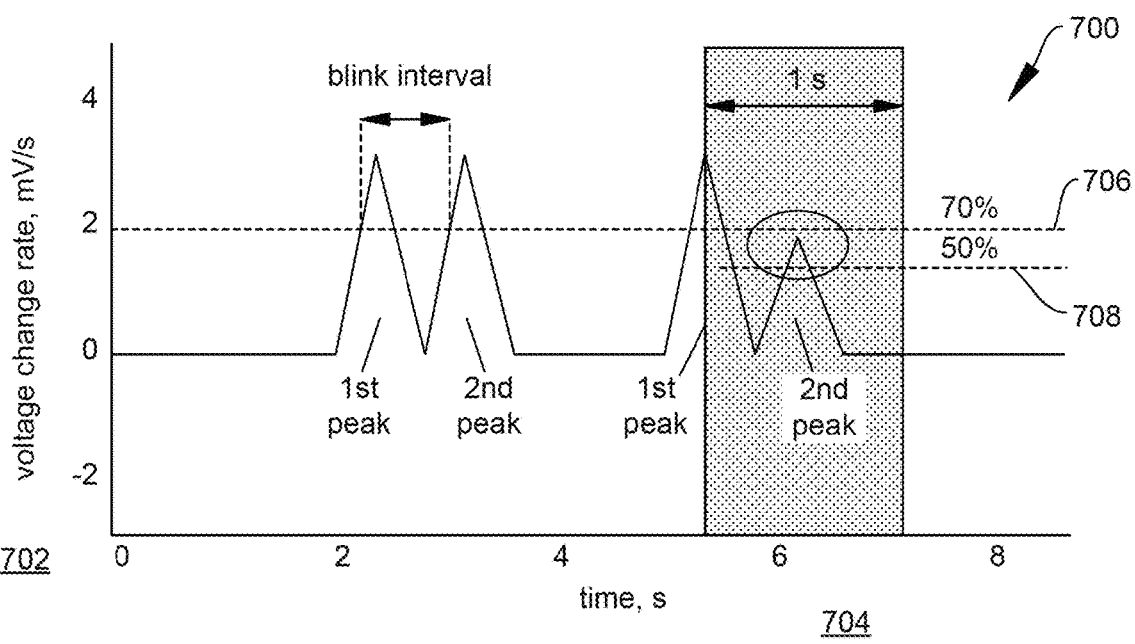
FIG. 7 is a graph as to blink burst, plotting voltage change over time 704.

FIG. 7 shows a graph 700 as to blink burst, plotting voltage change 702 over time 704. The graph 700 shows a voltage change rate when a user displays two blink bursts. A blink burst can be detected using a threshold 706 of 70%. The ability to detect such intervals can provide that microservice 126 to identify blink bursts.

It may be inferred that a gradual decrease in voltage reaction quantity occurs each time the user blinks, generating a smaller second peak of a blink burst. Therefore, detection of the second peak can be detected can be performed, where a new threshold is used to detect the second peak after the first. A threshold 708 of 50% threshold for the voltage change is used for the second blink after the first blink of a burst is detected.

Figure 8:
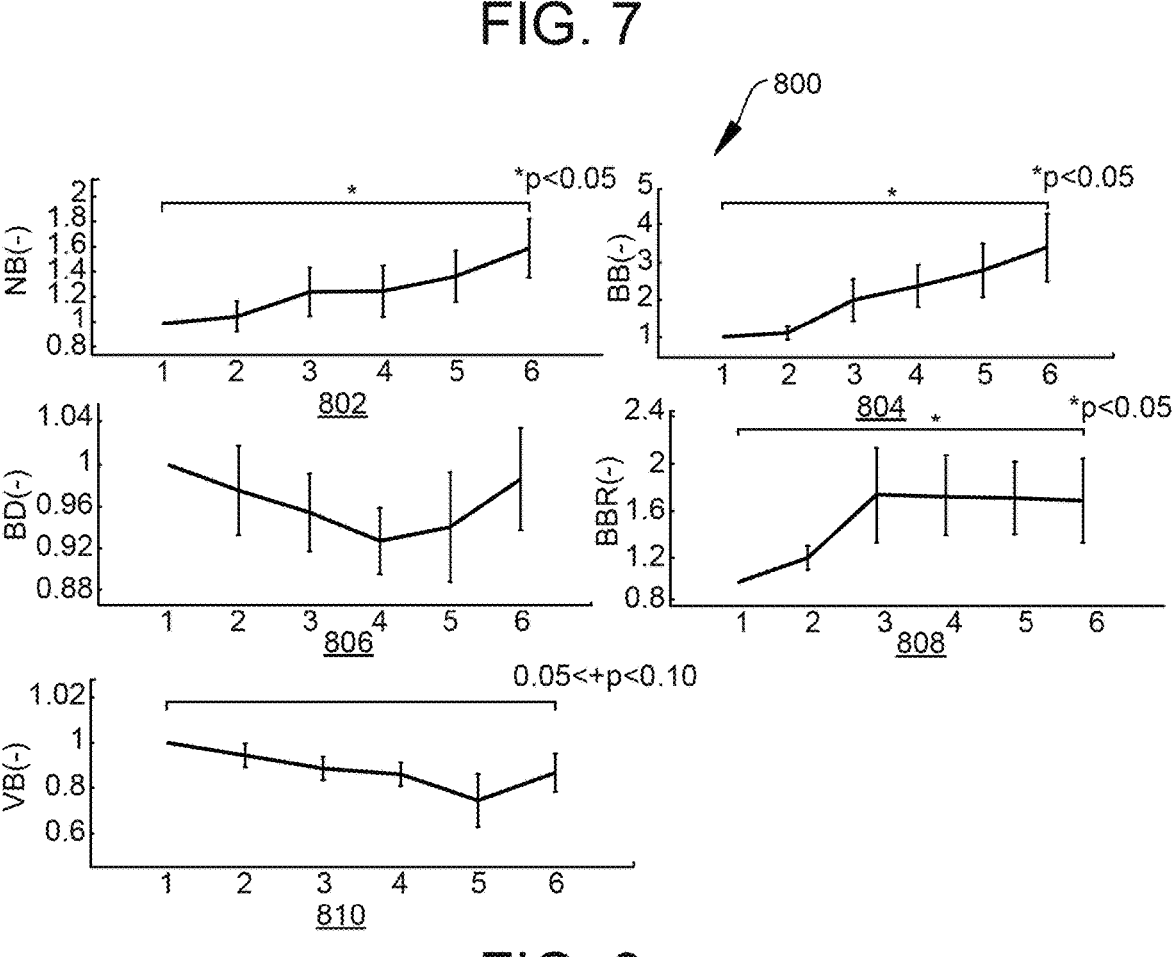
FIG. 8 are graphs of different user blink parameters.

FIG. 8 shows graphs of different user blink parameters. When all data is collected and analyzed by the microservice 126, various graphs of blink parameters can be generated. Such parameters can include number of blinks or NB, blink burst of a user's eye or BB, blink duration or BD, blink burst rate or BBR, and velocity of blink or VB.

Graph 802 shows NB time series variations. A gradual increase of NB is confirmed and there is a significant difference between the first and sixth sets (p=0.008). It can be inferred that the NB parameter is related to mental fatigue.

Graph 804 is observed BB time series variations. A gradual increase of BB is observed, and significant differences between the first and the sixth fatigue evaluation sets is seen (p=0.009). Therefore, it can be said that BB parameter correlates with mental fatigue.

Graph 806 is BD time series variations. BD decreases until a fourth set and then increases. This can infer that the eye closure time recovers after 40 min of the fatigue evaluation test, and no significant differences between the first and 6th sets were observed. This can indicate that it is uncertain whether BD is related to mental fatigue.

Graph 808 is BBR time series variations. It is seen that BBR increases rapidly until the third set, and then remains flat until the sixth set. A significant difference between the first and sixth sets can be confirmed (p=0.032). An inference can be made that BBR is related to changes in user alertness. No significant difference is seen after the third set of fatigue evaluations, even though this parameter rapidly increases during the first 30 min of testing.

Graph 810 is VB time series variation. A slight decrease in the VB parameter can be seen, and there is a significant trend between the first and sixth sets of the test (p=0.066). Therefore, an inference can be made that VB provides a mental fatigue indicator.

Figure 9:
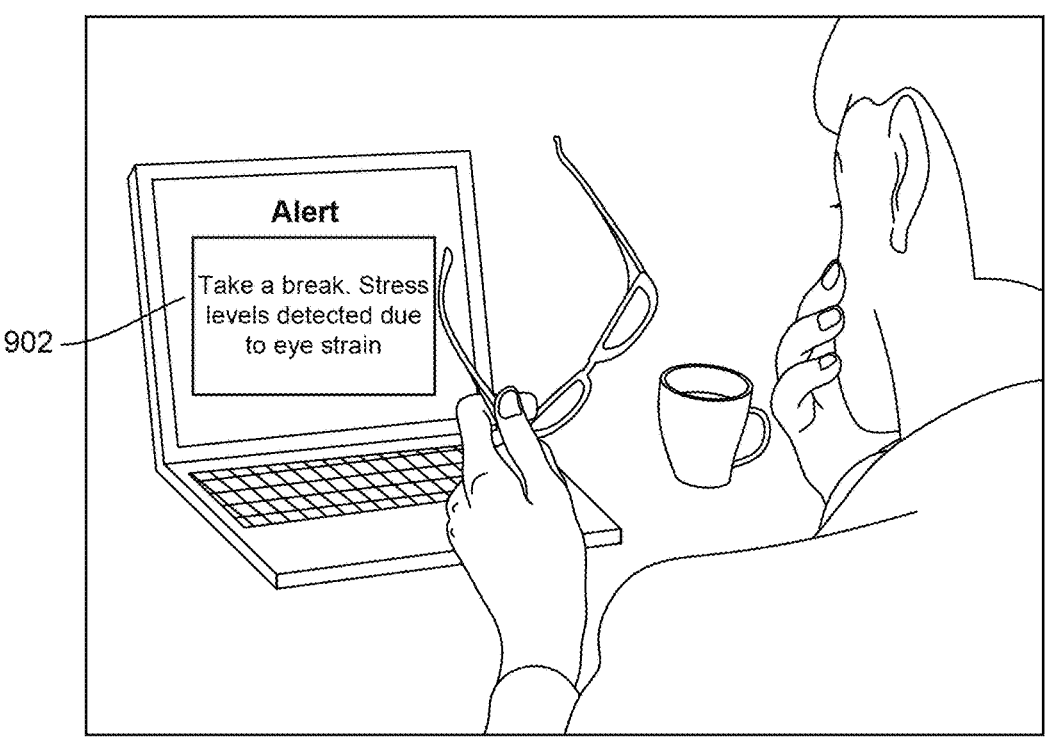
FIG. 9 is a user pop-up alert message.

FIG. 9 shows a user pop-up alert message. At stage 212 of FIG. 2, if mental fatigue is determined to be at threshold, a pop-up message 902 is presented to a user to take a break or to suggest a strain reducing activity.

At stage 214 of FIG. 2, if the user neglects the warning of stage 212, and continues activity, this can increase the strain level beyond the threshold limit. The user microservice 126 can classify the user as "over-stressed." Once fatigue index or mental strain level increases beyond the threshold limit, microservice 126 classifies the user as an "over-stressed" and generates an alert for the operating system 122 to take necessary action to prevent the user from increasing the stress beyond the current state.

Figure 10:
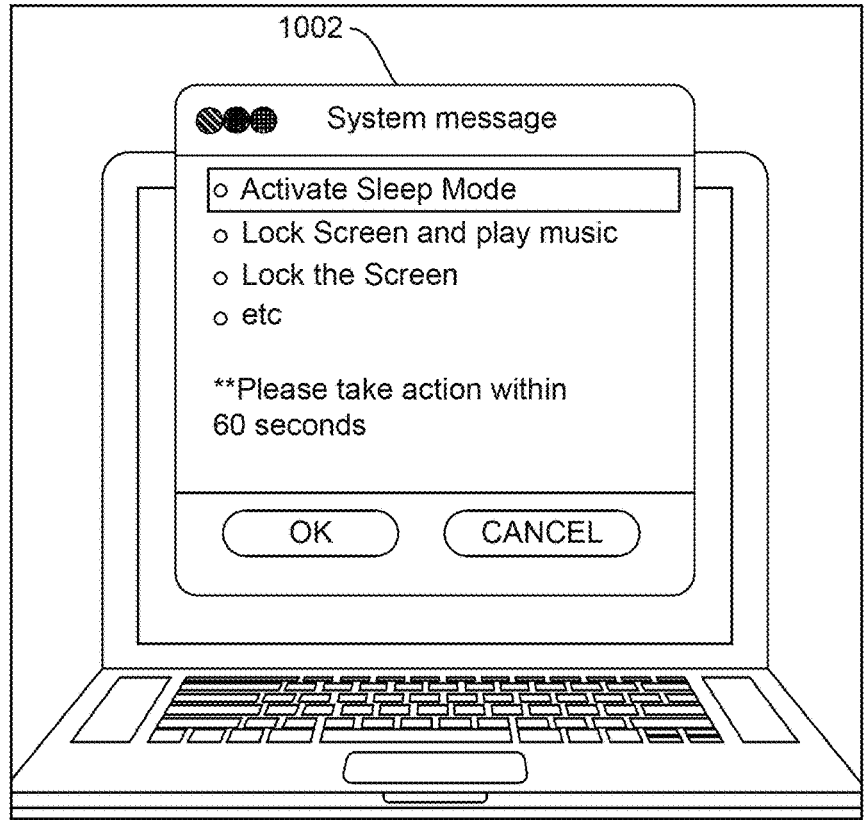
FIG. 10 is a pop-up message as to automatically taking corrective action.

FIG. 10 shows a pop-up message 1002 as to automatically taking corrective action. When the operating system 122 gets the alert from microservice 126, the operating system 122 can trigger pop-up message 1002 to display options from which the user must choose from, such as "lock screen and play music," "activate sleep mode," etc. Other options can be made available to allow the user to take a break and relax. In certain implementations, if an option is not chosen after a certain time after pop-up message 1002, automatic corrective action, such as triggering sleep mode, is taken.

FIG. 11 is a chart 1100 of microservice 126 interaction based on different levels of monitoring. Implementations can provide for the microservice 126 to provide various interactions based on a monitoring mode 1102. Monitoring mode 1102 can include a light mode 1104, a medium mode 1106, and high mode 1108. Different engagement 1110 levels (level 1, level 2, level 3) can be performed by microservice 126 model based on monitoring mode (light mode 1104, a medium mode 1106, and high mode 1108). Furthermore, different resolutions 1112 can be performed by microservice 126 model based on monitoring mode (light mode 1104, a medium mode 1106, and high mode 1108).

Figure 12:
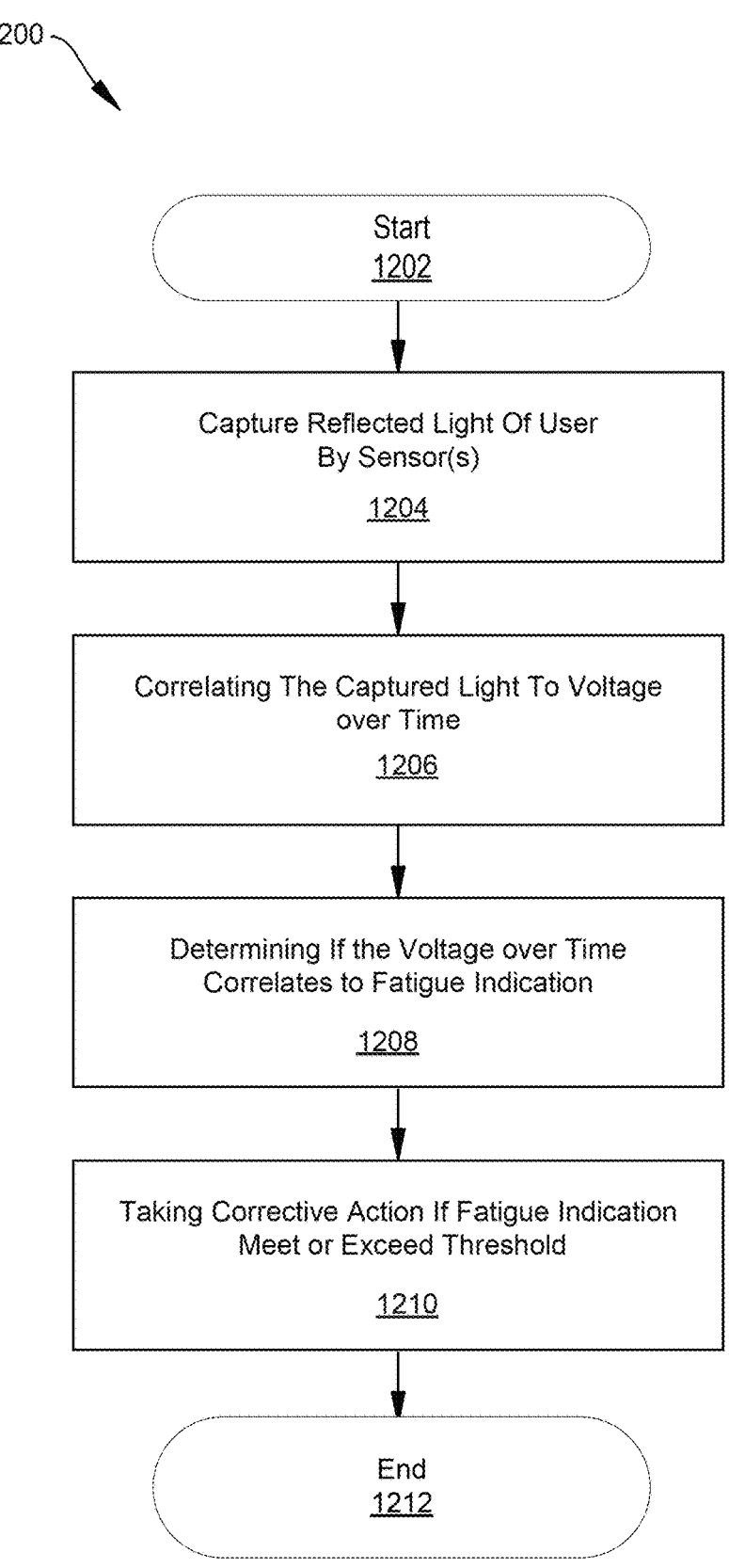
FIG. 12 is a general flowchart for assessing and reducing mental strain of users when operating information handling systems.

FIG. 12 is a generalized flowchart 1200 for assessing and reducing mental strain of users when operating information handling systems. The order in which the method is described is not intended to be construed as a limitation, and any number of the described method steps may be combined in any order to implement the method, or alternate method. Additionally, individual steps may be deleted from the method without departing from the spirit and scope of the subject matter described herein. Furthermore, the method may be implemented in any suitable hardware, software, firmware, or a combination thereof, without departing from the scope of the invention.

At step 1202 the process 1200 starts. At step 1204, light reflected from a user is captured by sensor(s) 106 of the information handling system 100. At step 1206, the captured light is converted to voltage values over time to determine eye movement and blinking as discussed herein. At step 1208, a determination is performed as to voltage values over time correlate to fatigue. In particular, voltage values over time as to eye movement and blinking can correlate or indicate fatigue. At step 1210, corrective action is taken if determined fatigue values meet or exceed a threshold. At step 1212, the process 1200 ends.

As will be appreciated by one skilled in the art, the present invention may be embodied as a method, system, or computer program product. Accordingly, embodiments of the invention may be implemented entirely in hardware, entirely in software (including firmware, resident software, microcode, etc.) or in an embodiment combining software and hardware. These various embodiments may all generally be referred to herein as a "circuit," "module," or "system." Furthermore, the present invention may take the form of a computer program product on a computer-usable storage medium having computer-usable program code embodied in the medium.

Any suitable computer usable or computer readable medium may be utilized. The computer-usable or computer-readable medium may be, for example, but not limited to, an electronic, magnetic, optical, electromagnetic, infrared, or semiconductor system, apparatus, or device. More specific examples (a non-exhaustive list) of the computer-readable medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, or a magnetic storage device. In the context of this document, a computer-usable or computer-readable medium may be any medium that can contain, store, communicate, or transport the program for use by or in connection with the instruction execution system, apparatus, or device.

Computer program code for carrying out operations of the present invention may be written in an object-oriented programming language such as Java, Smalltalk, C++ or the like. However, the computer program code for carrying out operations of the present invention may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

Embodiments of the invention are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The present invention is well adapted to attain the advantages mentioned as well as others inherent therein. While the present invention has been depicted, described, and is defined by reference to particular embodiments of the invention, such references do not imply a limitation on the invention, and no such limitation is to be inferred. The invention is capable of considerable modification, alteration, and equivalents in form and function, as will occur to those ordinarily skilled in the pertinent arts. The depicted and described embodiments are examples only and are not exhaustive of the scope of the invention.

Skilled practitioners of the art will recognize that many such embodiments are possible, and the foregoing is not intended to limit the spirit, scope or intent of the invention. Consequently, the invention is intended to be limited only by the spirit and scope of the appended claims, giving full cognizance to equivalents in all respects.

What is claimed is:

1. A computer-implementable method executed by an information handling system comprising a processor, memory, display, and one or more dye-sensitive photoelectric sensors integrated into the display, the method comprising:

capturing, by the dye-sensitive photoelectric sensors, light emitted from the display, reflected light from an eye of the user;

training the microservice of the information handling system with an initial data set that defines intensity of light based on captured reflected light;

converting intensity differences in the reflected light to time-series voltage values;

classifying, by the microservice, the time-series voltage values into opened-eye, blinked-eye, and closed-eye states based on voltage amplitude thresholds;

detecting spontaneous blinks and blink bursts by applying a first voltage change-rate threshold to detect an initial blink and a second voltage change-rate threshold lower than the first threshold to detect a subsequent blink within a burst;

calculating a fatigue index based on one or more parameters comprising number of blinks, blink burst rate, blink duration, and blink velocity over a defined monitoring interval; and taking corrective action if the fatigue index meets or exceeds a fatigue threshold in regards to defined intensity of light, by transmitting an alert from the microservice to an operating system of the information handling system.

2. The method of claim 1, wherein the converting occurs when the user looks at the display of the information handling system.

3. The method of claim 1, wherein the classifying, by the microservice, is related to decrease or increase of voltage values.

4. The method of claim 1, wherein the classifying, by the microservice includes parameters as to blinking includes one or more of number of blinks, blink burst of the user's eye, blink duration, blink burst rate, and velocity of blink.

5. The method of claim 1, wherein the classifying, by the microservice is defined by a detection rate percentage that equals number of blinks divided by average medically determined blinks.

6. The method of claim 1, wherein the taking of corrective action is based on different levels of monitoring.

7. A system comprising:

a processor;

a data bus coupled to the processor; and a non-transitory, computer-readable storage medium embodying computer program code, the non-transitory, computer-readable storage medium being coupled to the data bus, the computer program code interacting with a plurality of computer operations for assessing and reducing mental strain of a user when operating an information handling system executable by the processor and configured for:

capturing, by one or more dye-sensitive photoelectric sensors of a display of the information handling system, light emitted from the display, reflected light from an eye of the user;

training a microservice of the information handling system with an initial data set that defines intensity of light based on captured reflected light;

converting intensity differences in the reflected light to time-series voltage values;

classifying, by the microservice, the time-series voltage values into opened-eye, blinked-eye, and closed-eye states based on voltage amplitude thresholds;

detecting spontaneous blinks and blink bursts by applying a first voltage change-rate threshold to detect an initial blink and a second voltage change-rate threshold lower than the first threshold to detect a subsequent blink within a burst:

calculating a fatigue index based on one or more parameters comprising number of blinks, blink burst rate, blink duration, and blink velocity over a defined monitoring interval; and taking corrective action if the fatigue index meets or exceeds a fatigue threshold in regards to defined intensity of light, by transmitting an alert from the microservice to an operating system of the information handling system.

8. The system of claim 7, wherein the captured reflective light accounts for light generated by the display of the information handling system.

9. The system of claim 7, wherein the converting occurs when the user looks at the display of the information handling system.

10. The system of claim 7, wherein the classifying, by the microservice, is related to decrease or increase of voltage values.

11. The system of claim 7, wherein the classifying, by the microservice includes parameters as to blinking includes one or more of number of blinks, blink burst of the user's eye, blink duration, blink burst rate, and velocity of blink.

12. The system of claim 7, wherein the classifying, by the microservice is defined by a detection rate percentage that equals number of blinks divided by average medically determined blinks.

13. The system of claim 7, wherein the taking of corrective action is based on different levels of monitoring.

14. A non-transitory, computer-readable storage medium embodying computer program code for assessing and reducing mental strain of a user when operating an information handling system, the computer program code comprising computer executable instructions configured for:

capturing, by one or more dye-sensitive photoelectric sensors of a display of the information handling system, light emitted from the display, reflected light from an eye of the user;

training a microservice of the information handling system with an initial data set that defines intensity of light based on captured reflected light;

converting intensity differences in the reflected light to time-series voltage values;

classifying, by the microservice, the time-series voltage values into opened-eye, blinked-eye, and closed-eye states based on voltage amplitude thresholds;

detecting spontaneous blinks and blink bursts by applying a first voltage change-rate threshold to detect an initial blink and a second voltage change-rate threshold lower than the first threshold to detect a subsequent blink within a burst;

calculating a fatigue index based on one or more parameters comprising number of blinks, blink burst rate, blink duration, and blink velocity over a defined monitoring interval; and taking corrective action if the fatigue index meets or exceeds a fatigue threshold in regards to defined intensity of light, by transmitting an alert from the microservice to an operating system of the information handling system.

15. The non-transitory, computer-readable storage medium of claim 14, wherein the classifying, by the microservice is defined by a detection rate percentage that equals number of blinks divided by average medically determined blinks.

16. The non-transitory, computer-readable storage medium of claim 14, wherein the classifying, by the microservice, is related to decrease or increase of voltage values.

17. The non-transitory, computer-readable storage medium of claim 14, wherein the classifying, by the microservice includes parameters as to blinking includes one or more of number of blinks, blink burst of the user's eye, blink duration, blink burst rate, and velocity of blink.

18. The non-transitory, computer-readable storage medium of claim 14 further comprising taking corrective action of the information handling system based on different levels of monitoring.

* * * * *